US010656129B2

(12) United States Patent
Hsueh et al.

(10) Patent No.: US 10,656,129 B2
(45) Date of Patent: *May 19, 2020

(54) MINIATURE GAS SENSOR (71) Applicant: NATIONAL APPLIED RESEARCH LABORATORIES, Taipei (TW)

(72) Inventors: Ting-Jen Hsueh, Tainan (TW); Yu-Jen Hsiao, Tainan (TW); Yu-Te Lin, Tainan (TW); Yen-Hsi Li, Tainan (TW); Yung-Hsiang Chen, Tainan (TW); Jia-Min Shieh, Hsinchu (TW)

(73) Assignee: NATIONAL APPLIED RESEARCH LABORATORIES, Taipei (TW)

( * ) Notice: Subject to any disclaimer, the term of this patent is extended or adjusted under 35 U.S.C. 154(b) by 139 days.

This patent is subject to a terminal disclaimer.

(21) Appl. No.: 15/837,227

(22) Filed: Dec. 11, 2017

(65) Prior Publication Data

US 2019/0178860 A1 Jun. 13, 2019

(51) Int. Cl.
*G01N 27/12* (2006.01)
*G01N 33/00* (2006.01)
*G01N 21/3504* (2014.01)
*G01N 27/62* (2006.01)
*G01N 21/359* (2014.01)

(52) U.S. Cl.
CPC ..... *G01N 33/0009* (2013.01); *G01N 21/3504* (2013.01); *G01N 21/359* (2013.01); *G01N 27/12* (2013.01); *G01N 27/123* (2013.01); *G01N 27/125* (2013.01); *G01N 27/626* (2013.01)

(58) Field of Classification Search
CPC .... G01N 27/12; G01N 27/125; G01N 27/126; G01N 27/127; G01N 27/128
See application file for complete search history.

(56) References Cited

U.S. PATENT DOCUMENTS

| 5,147,523 | A | * | 9/1992 | Yagawara | G01N 27/12 |
| | | | | | 204/424 |
| 2006/0154401 | A1 | * | 7/2006 | Gardner | G01N 27/128 |
| | | | | | 438/53 |
| 2006/0196248 | A1 | * | 9/2006 | Nakano | G01N 27/125 |
| | | | | | 73/31.06 |
| 2014/0209983 | A1 | * | 7/2014 | Burgi | G01N 27/128 |
| | | | | | 257/253 |
| 2014/0225115 | A1 | * | 8/2014 | Tai | H01L 21/02491 |
| | | | | | 257/49 |
| 2017/0370865 | A1 | * | 12/2017 | Samarao | C23C 16/45525 |
| 2018/0356357 | A1 | * | 12/2018 | Samarao | G01N 27/127 |

\* cited by examiner

*Primary Examiner* — Herbert K Roberts
(74) *Attorney, Agent, or Firm* — Rosenberg, Klein & Lee (57) ABSTRACT

The present invention provides a miniature gas sensor, which comprises a gas sensor chip. The gas sensor chip includes a hollow structure on the back. An insulating layer is disposed below the sensing material. A miniature heating device is disposed surrounding the sensing material. The sensing material is adhered to the sensing electrodes. The sensing material includes two metal oxide semiconductors or a compound structure of the sensing layer having a metal oxide semiconductor and a reaction layer with a rough surface. An interface layer is sandwiched between the two metal oxide layers for increasing the efficiency in sensing gas. The gas sensor according to the present invention can be implemented on silicon substrate with hollow structures. In addition, the size of the chip can be miniaturized.

22 Claims, 8 Drawing Sheets

MINIATURE GAS SENSOR

FIELD OF THE INVENTION

The present invention relates generally to a gas sensor and the method for manufacturing the same, and particularly to a miniature gas sensor and the method for manufacturing the same.

BACKGROUND OF THE INVENTION

Following the evolution path of social commercialization and industrialization, increasing indoor space is utilized and more carriers are used for satisfying people's needs in rest, work, and commute. Nonetheless, when people are situated in closed indoor space, accumulation of hazardous gas will occur due to air noncirculation. At best, the living quality of the people in the space will be affected. At worst, it may hurt human bodies directly. In general, when the indoor concentration of carbon dioxide is below 1,000 ppm, it is considered normal and the air circulation is good. As the indoor concentration of carbon dioxide is raised to 1,000 ppm~2,000 ppm, oxygen is insufficient. People may feel tired and become anxious. When the indoor concentration of carbon dioxide is further increased above 5,000 ppm, anoxia may occur, leading to permanent brain injury, coma, or even death. In actual daily measurement, owing to insufficient air exchange of the indoor air conditioner or excessive number of people in the space, the actual measurement of carbon dioxide concentration can reach around 2,000 ppm~3,000 ppm, which is a condition making people feel drowsy or slight uncomfortable. In a further action for controlling the indoor concentration of carbon dioxide is not performed, it may continue to rise. Then the people in the space are exposed to danger.

On the other hand, carbon monoxide is the gas requiring more monitoring and control in our daily lives. Carbon monoxide is a colorless and smell-less chemical formed by incomplete combustion of carbon-containing substances. Thereby, the incomplete combustion of fuel gas or motorcycle exhaust makes people to be exposed to carbon monoxide in the living environment. Because the affinity of hemoglobins with carbon monoxide is higher than with oxygen by two to three hundred times, when a human inhales carbon monoxide, it will compete with the oxygen in the body for the possibility of combining with hemoglobins. It replaces oxygen and combines with hemoglobins. The oxygen level in human blood decreases. People will lose consciousness, become stuporous gradually without notice and eventually die owing to heart and brain damages. Given the threat on lives of carbon monoxide, early detection of increases in carbon monoxide in closed space becomes a crucial subject.

The current commercial gas sensors are mainly infrared gas sensors. The infrared supplies energy for exciting gas and producing changes in temperature, displacement, or frequency. According to the absorption of infrared by gas and detecting the characteristic absorption peaks, the type and concentration of gas can be judged. Although the accuracy sensing gas using infrared is high, it is sensitive to ambient temperature. Besides, due to its large size, high cost, and difficulty in miniaturization, the promotion of infrared gas sensors is challenging.

In addition, there is another gas sensor that detects gas by using semiconductors. Metal-oxide materials are sintered to form semiconductors. By keeping the heater at a high temperature, semiconductor metal oxides contact an inflammable gas. Once the resistance is related to the gas concentration, the detection for carbon monoxide can be achieved. Although the device is simple for monitoring, the circuitry is vulnerable to temperature and humidity. Besides, the accuracy of the sensor is also vulnerable to the thermoelectric effect of semiconductors.

Based on the above description, it is understood that the detection of gas concentration is closely related to the safety of indoor space. Unfortunately, current commercial gas sensors are limited in functions. Accordingly, how to provide a miniature and accurate gas sensor has become the major technical challenge in the field.

SUMMARY

An objective of the present invention is to provide a miniature gas sensor, which is small, sensitive, and applicable to various closed space, portable devices, or vehicles.

Another objective of the present invention is to provide a miniature gas sensor. The sensing materials used in the miniature gas sensor are highly sensitive so that the required sensing temperature of the sensing layer is be lowered effectively and hence avoiding bad influences of heat in the sensing process.

A further objective of the present invention is to provide a method for manufacturing a miniature gas sensor. By using the method, sensing materials can be coated to a substrate with excellent adhesion and thickness control.

In order to achieve the above objectives, the present invention discloses a miniature gas sensor, which comprises a substrate, a dielectric layer, and a sensing layer. The dielectric layer is disposed on the substrate, and includes a heating device and two electrodes. The sensing layer is disposed on the heating device and connected with the two electrodes. Besides, the sensing layer includes a metal oxide layer and a reaction layer. The reaction layer is disposed on the metal oxide layer. The surface of the reaction layer is a rough surface.

According to an embodiment of the present invention, the heating device and the two electrodes can be further disposed on the dielectric layer.

According to an embodiment of the present invention, the substrate is a discontinuous structure such that the dielectric layer is disposed on the substrate with hollow portions and producing a heat dissipating region not contacting directly with the substrate.

According to an embodiment of the present invention, the material of the reaction layer is selected from the group consisting of lanthanum carbonate and nanometer gold.

According to an embodiment of the present invention, the material of the metal oxide layer is selected from the group consisting of tungsten oxide, zinc oxide, and tin oxide.

According to an embodiment of the present invention, the material of the heating device is selected from the group consisting of titanium, platinum, silver, and tantalum.

According to an embodiment of the present invention, the material of the dielectric layer is selected from the group consisting of silicon nitride, silicon oxide, or silicon oxynitride.

In order to achieve the above objectives, the present invention further discloses a miniature gas sensor, which is a semiconductor gas sensor comprising a substrate, a dielectric layer, a heating device, two electrodes, and a sensing layer. The sensing layer is disposed on the heating device and connected with the two electrodes. In addition, the sensing layer includes a first metal oxide layer and a second metal oxide layer. The second metal oxide layer is disposed on the first metal oxide layer. The materials of the first and second metal oxide layers are tin oxide and tungsten oxide, respectively.

According to an embodiment of the present invention, the surface of the second metal oxide layer is a rough surface.

According to an embodiment of the present invention, the heating device and the two electrodes can be further disposed on the dielectric layer; the material of the heating device is selected from the group consisting of titanium, gold, platinum, silver, and tantalum.

According to an embodiment of the present invention, the substrate is a discontinuous structure such that the dielectric layer is disposed on the substrate with hollow portions and producing a heat dissipating region not contacting directly with the substrate.

According to an embodiment of the present invention, a reaction layer is further disposed on the sensing layer.

According to an embodiment of the present invention, the heating device and the two electrodes can be further disposed on the dielectric layer.

According to an embodiment of the present invention, the material of the dielectric layer is selected from the group consisting of silicon nitride, silicon oxide, or silicon oxynitride.

According to an embodiment of the present invention, the first metal oxide layer further includes a nanometer metal layer on the surface.

According to an embodiment of the present invention, an interface layer is sandwiched between the first and second metal oxide layers.

According to an embodiment of the present invention, after thermal diffusion and phase change reactions with the tungsten oxide and zinc oxide of the first and second metal oxide layers, the interface layer forms a mixture having tungsten oxide and zinc oxide.

In order to achieve the above objectives, the present invention further discloses a miniature gas sensor, which is a semiconductor gas sensor comprising a substrate, one or more dielectric layer, and a sensing layer. The one or more dielectric layer is disposed on the substrate and includes a heating device and two electrodes. The sensing layer is disposed on the heating device and connected with the two electrodes. Besides, the sensing layer is formed by one or more first metal oxide layer. The stress of the dielectric layer is between 1 MPa and 20 MPa.

According to an embodiment of the present invention, the material of the sensing layer is zinc oxide or tungsten oxide.

According to an embodiment of the present invention, the material of the dielectric layer is selected from the group consisting of silicon nitride, silicon oxide, or silicon oxynitride.

According to an embodiment of the present invention, the surface of the second metal oxide layer is a rough surface.

According to an embodiment of the present invention, the first metal oxide layer further includes a nanometer metal layer on the surface.

According to an embodiment of the present invention, the material of the nanometer metal layer is selected from the group consisting of titanium, gold, platinum, silver, palladium, and tantalum.

According to an embodiment of the present invention, the thickness of the dielectric layer is between 2000 and 25000 angstroms.

DETAILED DESCRIPTION

In order to make the structure and characteristics as well as the effectiveness of the present invention to be further understood and recognized, the detailed description of the present invention is provided as follows along with embodiments and accompanying figures.

According to the present invention, a novel miniature gas sensor is provided to solve the problem of large size, high price, difficulty in miniaturization, and inaccuracy in current gas sensors. By using a semiconductor structure as the basis for the miniature gas sensor, the volume of a gas sensor can be reduced effectively and thus improving its utilization. In addition, the present invention includes a reaction layer, which adopts lanthanum carbonate or nanometer gold as the sensing material for the semiconductor gas sensor. Alternatively, the present invention includes two metal oxide layers, which adopts zinc oxide or tungsten oxide as the sensing material for the semiconductor gas sensor. Thereby, different gases can be sensed. Moreover, the sensitivity of the gas sensor can be enhanced, and hence improving the accuracy of the gas sensor.

Accordingly, the present invention provides a novel miniature gas sensor using a semiconductor gas sensor as the basis. The semiconductor structure includes a heating device. By disposing a sensing layer on the heating device, the lanthanum carbonate or nanometer gold in the reaction layer of the sensing layer contacts the gas, reacts, and generates ionized electrons. Because the reaction of lanthanum carbonate or nanometer gold with gas is extremely sensitive, the potential changes can be measured by the heating device easily. Then the gas concentration can be estimated according to the resistance changes. Hence, high-sensitivity detection can be achieved.

In the following, the components and properties of the miniature gas sensor according to the present invention will be further described.

Figure 1:
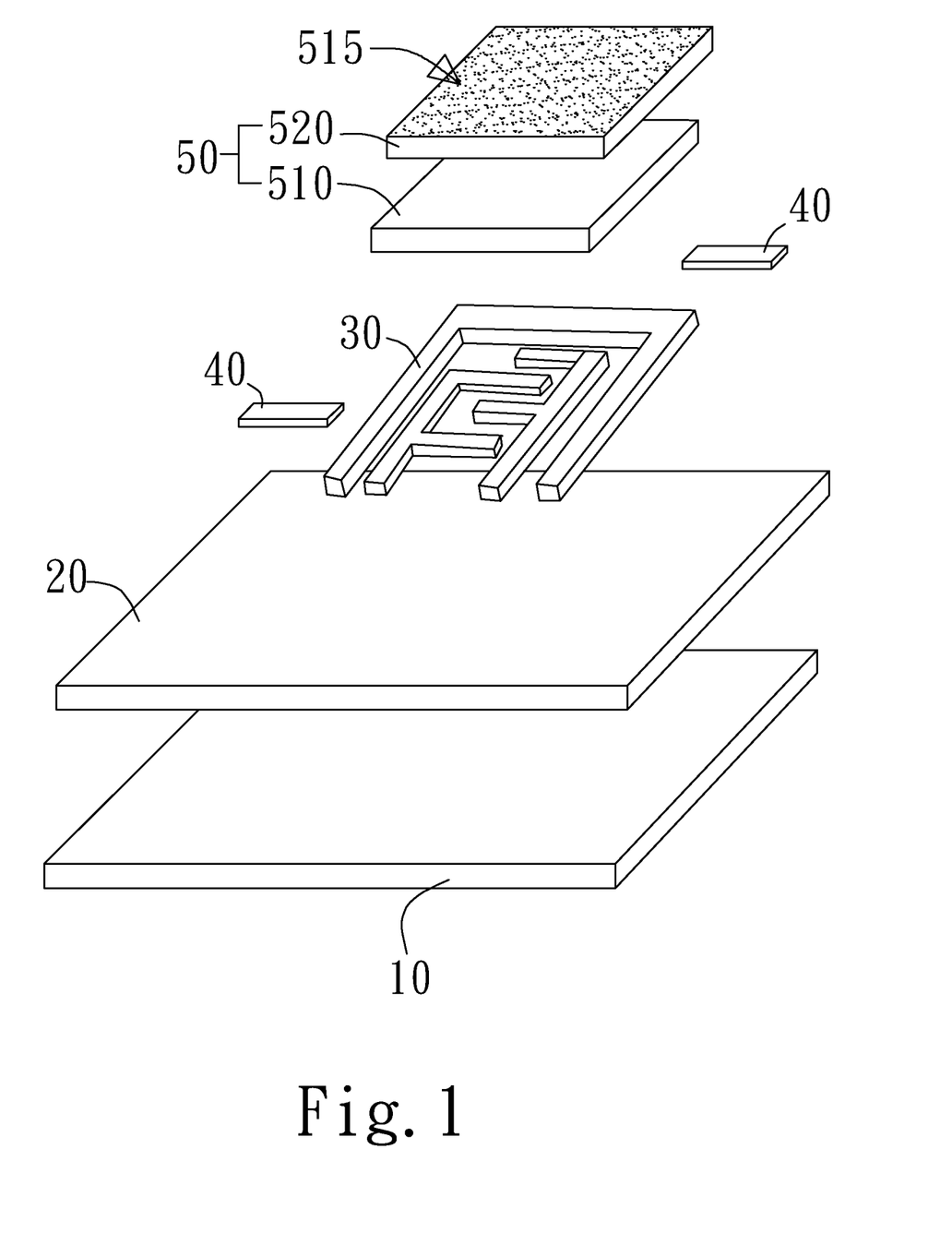
FIG. 1 shows a side exploded view according to a preferred embodiment of the present invention.

Please refer to FIG. 1, which shows a side exploded view according to a preferred embodiment of the present invention. As shown in the figure, the present invention provides a substrate 10 and a dielectric layer 20. The dielectric layer 20 is disposed on the substrate 10 and includes a heating device 30 and two electrodes 40. Next, a sensing layer 50 is disposed on the heating device 30 and connected with the two electrodes 40. The sensing layer 50 includes a first metal oxide layer 510 and a reaction layer 520. The reaction layer 520 is disposed on the first metal oxide layer 510. The surface of the reaction layer 520 is a rough surface 515 for increasing the contact area for sensing gas and reaction efficiency.

Base on the above sensor, by providing different materials for the reaction layer 520, the gas sensor according to the present invention can sense different gasses, as described in the following.

When the material of the reaction layer 520 in the miniature gas sensor according to the present invention is lanthanum carbonate, carbon dioxide can be detected. When the oxygen ions ($O^{2-}$) in the air reacts with high-concentration carbon dioxide, carbonate ions ($CO_3^{2-}$) will be formed, as shown in Equation 1. At this moment, the carbonate ions will contact and react with the lanthanum carbonate in the reaction layer 520 to produce lanthanum carbonate, oxygen, carbon dioxide, and ionized electrons, as shown in Equation 2. Then the ionized electrons will increase the surface conductivity of the sensing layer 50 and reduce the resistivity. Because the resistance will drop as the ambient concentration of carbon dioxide increases, the ambient concentration of carbon dioxide can be estimated according to the change in resistance and thus achieving the purpose of the gas sensor. In addition, as the concentration of carbon dioxide in the air drops, the concentration of carbonate ions in the environment is insufficient to react with the lanthanum carbonate in the reaction layer 520 for producing electrons. Then, the ionized electrons in the sensing layer 50 during the sensing process will return to the reaction layer 520, and the resistance of the sensor will recover to the initial condition for next sensing of gas concentration.

$$CO_2 + O^{2-} \rightarrow CO_3^{2-} \quad \text{(Equation 1)}$$

$$La_2O_2CO_3 + CO_3^{2-} \rightarrow La_2O_2CO_3 + \tfrac{1}{2}O_2 + CO_2 + 2e^- \quad \text{(Equation 2)}$$

Furthermore, when the material of the reaction layer 520 in the miniature gas sensor according to the present invention is nanometer gold, carbon monoxide can be detected. As carbon monoxide is introduced and the temperature is raised, carbon monoxide will be decomposed into carbon dioxide and ionized electrons, as shown in Equation 3. The ionized electrons will increase the surface conductivity of the sensing layer 50 and reduce the resistivity. Likewise, because the resistance will drop as the ambient concentration increases, the ambient concentration of carbon monoxide can be detected effectively $$CO + O^{2-} \rightarrow CO_2 + 2e^- \quad \text{(Equation 3)}$$

The substrate 10 in the miniature gas sensor according to the present invention is used for carrying the semiconductor miniature gas sensor. To maintain the fundamental physical properties of substrate material during the manufacturing process, the substrate material with stability in high-temperature ambient is selected. In addition, to avoid influences of substrate material on the conductivity of the overall chip structure and misleading the conductivity of gas sensing, the substrate material is non-conductive. Based on the above properties, the substrate 10 provided by the present invention can be further selected from the group consisting of glass, silicon, and quartz.

The dielectric layer 20 in the miniature gas sensor according to the present invention is used for electrical isolation for the multilayer structure of semiconductor and increasing the sensing efficiency of the miniature gas sensor. The material of the dielectric layer 20 is an insulator in most cases. When an external electric field is applied, the electrons, ions, or molecules therein will be polarized and thus increasing the electrical capacity of the miniature gas sensor. Based on the above property, the dielectric layer 20 provided by the present invention can be further selected from the group consisting of silicon nitride, silicon oxide, and silicon oxynitride. Preferably, silicon nitride and silicon oxide are adopted and silicon nitride is coated on silicon oxide.

The dielectric layer 20 according to the present invention includes a heating device 30 and two electrodes 40 buried in the dielectric layer 20. Alternatively, they can be disposed on the dielectric layer 20 directly. The heating device 30 is connected with a power supply for receiving the electric power from the power supply and converting it to heat for the gas sensor according to the present invention. To supply stable heat, the material of the heating device 30 according to the present invention is mainly noble metals. Based on the above properties, the material of the heating device 30 is selected from the group consisting of titanium, platinum, gold, silver, and tantalum. In addition, the two electrodes 40 are electrically isolated from the heating device 30 and connected with the sensing layer 50 for measuring the changes in current and voltage of the sensing layer 50 produced by reactions and thus judging the ambient gas concentration.

The sensing layer 50 in the miniature gas sensor according to the present invention is used for contact and react with the target gas in the monitored environment. When the target gas contacts and reacts with the material of the sensing layer 50, the produced ionized electrons will change the potential of the sensing layer 50 and producing current. The two electrodes 40 connected with the sensing layer 50 perform measurement for sensing the gas. The sensing layer 50 includes a first metal oxide layer 510 and a reaction layer 520. The material of the reaction layer 520 and the reaction with the target gas have been described in the above. Hence, the details will not be repeated. In addition, the first metal oxide layer 510 according to the present invention is used as a conductor for conducting electrons. To make the function of transporting electrons more rapidly and agilely, the first metal oxide layer 510 according to the present invention adopts a single material. Based on the above description, the first metal oxide layer 510 according to the present invention is selected from the group consisting of tungsten oxide, zinc oxide, and tin oxide. The material of tungsten oxide can be tungsten trioxide ($WO_3$); the material of tin oxide can be tin dioxide ($SnO_2$).

Figure 2:
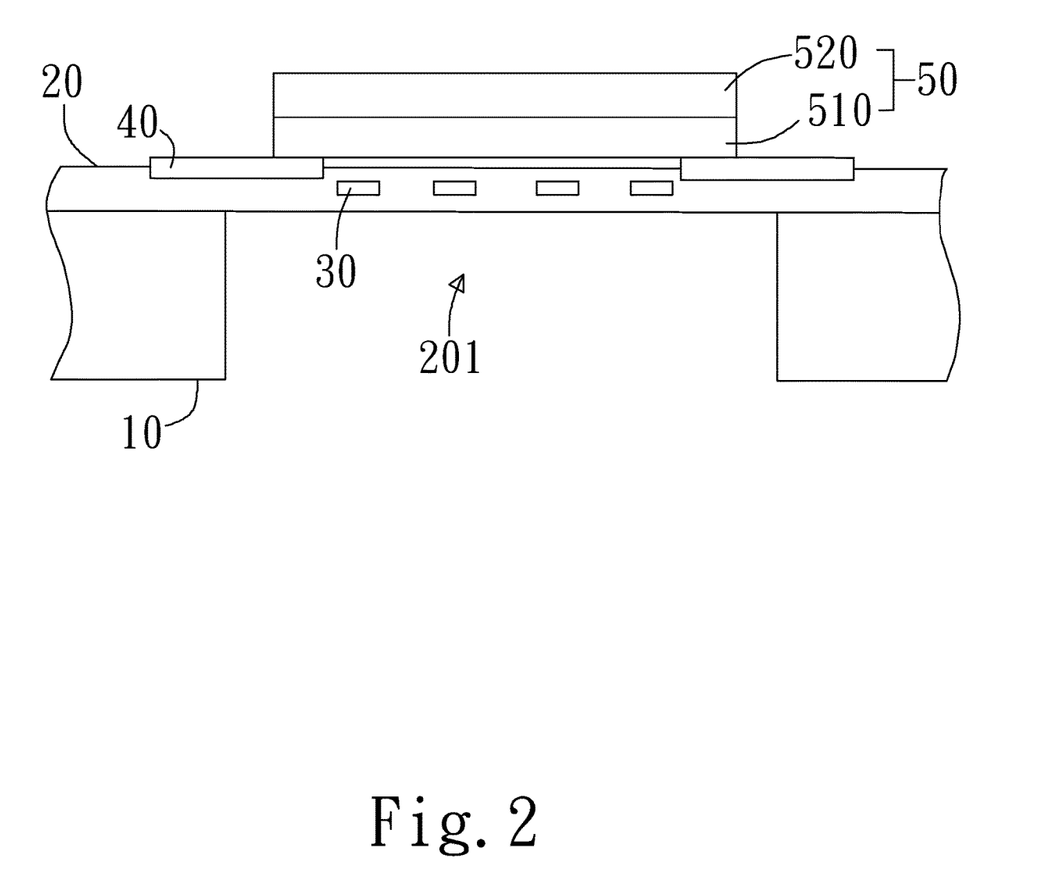
FIG. 2 shows a cross-sectional view according to another preferred embodiment of the present invention.

Please refer to FIG. 2, which shows a cross-sectional view according to another preferred embodiment of the present invention. As shown in the figure, the substrate 10 of the gas sensor is a discontinuous structure. By using the design, the dielectric layer 20 is disposed on the substrate 10 with hollow portions and producing a heat dissipating region 201 not contacting directly with the substrate 10. Thanks to the heat dissipating region 201, while the dielectric layer 20 is sensing gas, the heat generated by the heating device 30 can be regulated effectively and avoiding the overall temperature of the gas sensor from being too high. Consequently, the thermal electric effect can be reduced and the measurement stability and accuracy of the gas sensor can be enhanced.

In the following, embodiments are disclosed for describing the technical contents, characteristics, and results of the present invention. Nonetheless, the scope of the present invention is not limited to the embodiments.

Embodiment 1: Property Test on Lanthanum-Compound Miniature Gas Sensor

Figure 3A:
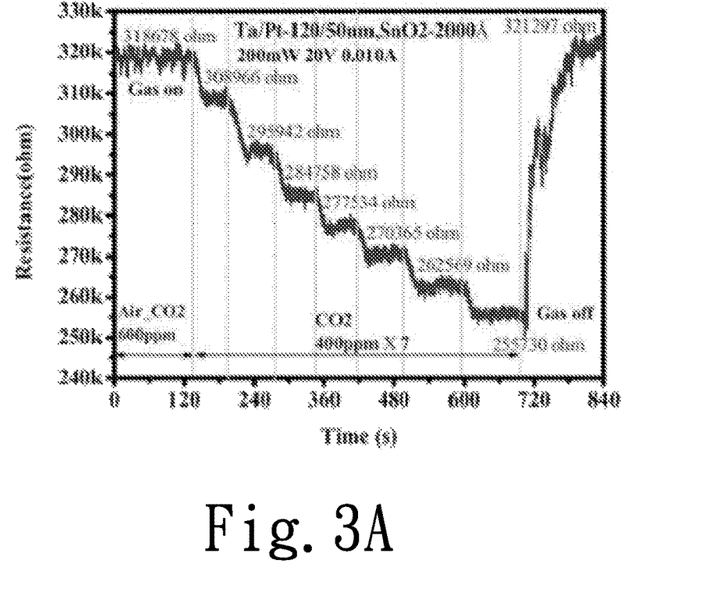
FIGS. 3A to 3C show schematic diagrams of the performance of the gas sensor according to a preferred embodiment of the present invention.

Please refer to FIG. 3A, which shows a schematic diagram of sensing time and resistance change while sensing carbon dioxide using a lanthanum-compound miniature gas sensor according to the present invention. As shown in the figure, in the first 120 seconds, the ambient concentration of carbon dioxide is 600 ppm. In the next 10 minutes, the ambient concentration of carbon dioxide is increased seven times. Each time, the ambient concentration of carbon dioxide is increased by 400 ppm. Observe the resistance change in the lanthanum-compound miniature gas sensor. According to the figure, each time the ambient concentration of carbon dioxide is increased, the resistance of the gas sensor will drop rapidly to a stable value. The stable value is maintained until the next increase of ambient concentration of carbon dioxide. The difference between the initial and final resistances can reach 60,000 ohm. It is apparent that the sensing capability if the gas sensor is stable and its sensing range is broad. Finally, when the supply of carbon diode is stopped and the ambient concentration of carbon dioxide is recovered to the initial condition, the resistance of the gas sensor can be recovered to the initial value in a short time. In addition, the recovered initial value is almost identical to the one prior to sensing. Consequently, the measurement stability of the gas sensor is high.

Figure 3B:
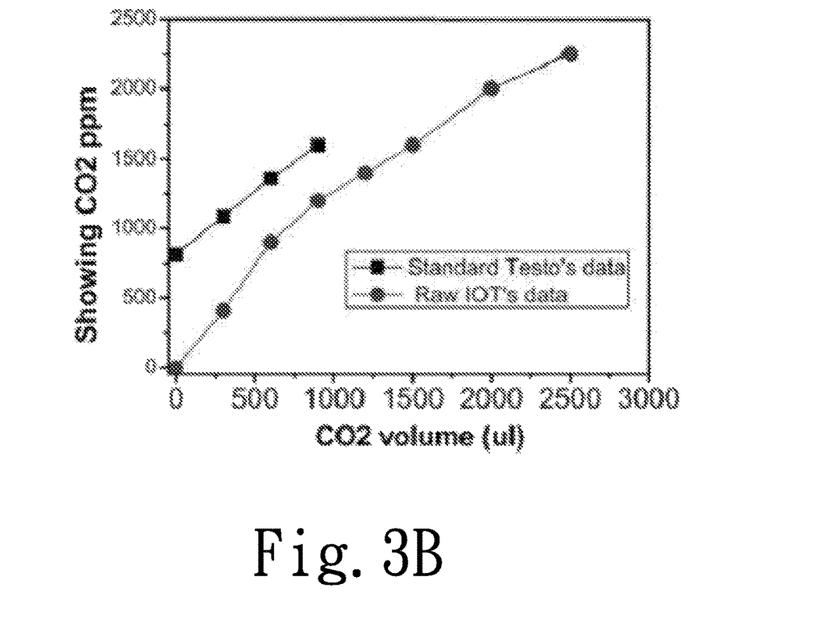

Please refer to FIG. 3B, which shows a comparison chart between the measurement result of the lanthanum-compound miniature gas sensor and the carbon dioxide sensor according to the prior art. The square points represent the results of a commercial carbon dioxide sensor; the circle points represent the results of the lanthanum-compound miniature gas sensor according to the present invention. As shown in the figure, the gas sensor provided by the present invention can sense a larger range of carbon-dioxide concentration; it is also more accurate. Apparently, the lanthanum-compound miniature gas sensor according to the present invention can make breakthrough in the technical challenges and provide a more sensitive and effective gas sensor for carbon dioxide.

Embodiment 2: Property Test on
Lanthanum-Compound Miniature Gas Sensor

Figure 3C:
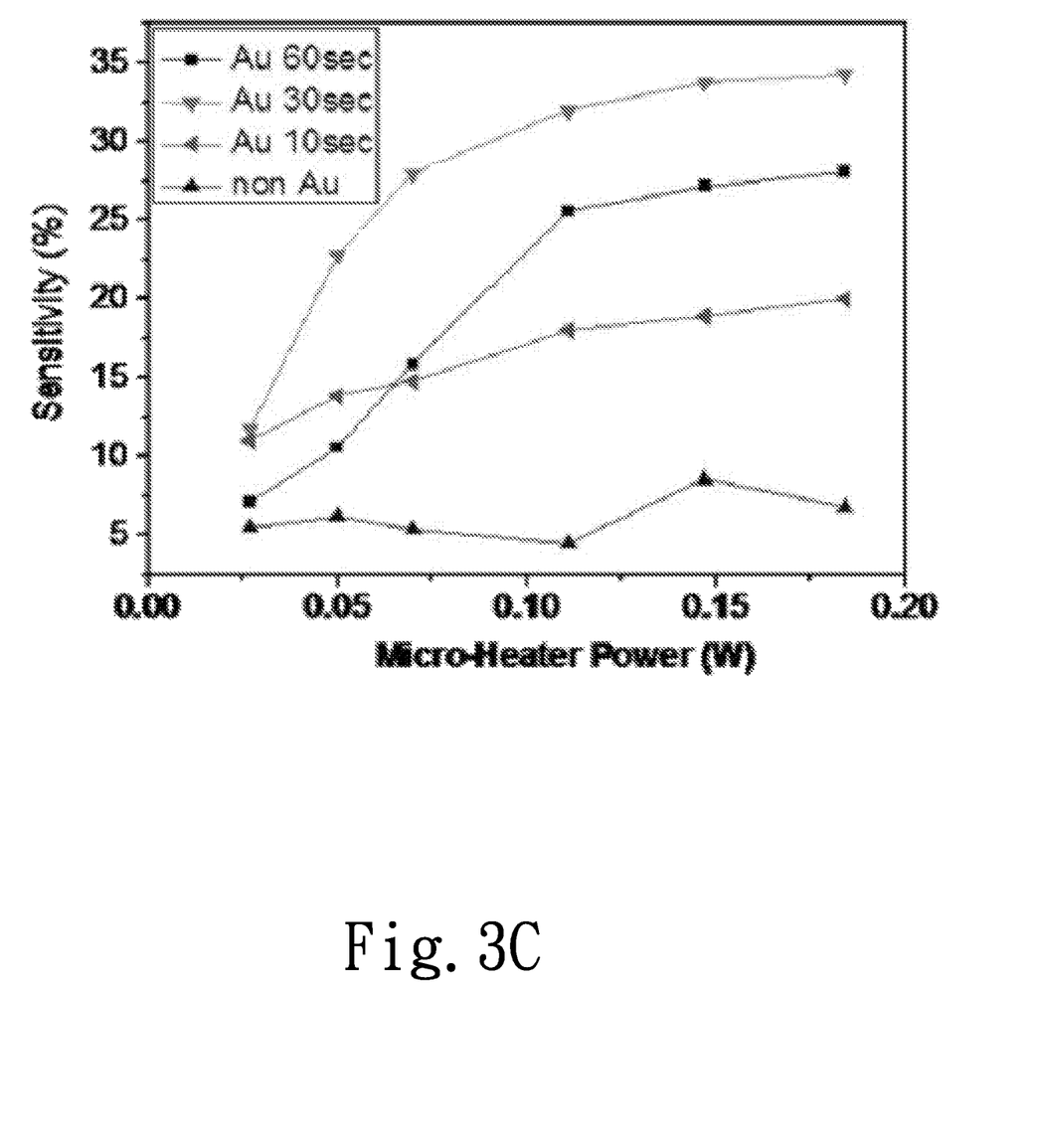

Please refer to FIG. 3C, which shows a trend chart between power and sensitivity for the nanometer-gold miniature gas sensor according to the present invention under different annealing conditions in a carbon monoxide ambient. As shown in the figure, when the gold-containing metal layer is not annealed, namely, when the time is at 0 second, because the gold-containing metal layer will not form nanometer gold dots, as the miniature gas sensor operates and the heating power increases, the capability of sensing gas will not increase. In addition, other gas sensors prepared by different annealing times own similar trends of resistance change. Nonetheless, the miniature gas sensor with annealing time of 30 second own the greatest sensitivity (~35%); its change trend is more stable than those with 15 and 60 seconds of annealing time. Obviously, the distribution of nanometer gold dots is the most complete and appropriate for absorbing more carbon monoxide. Besides, in the measurement range, nanometer gold dots can give the highest and most accurate values.

Figure 4:
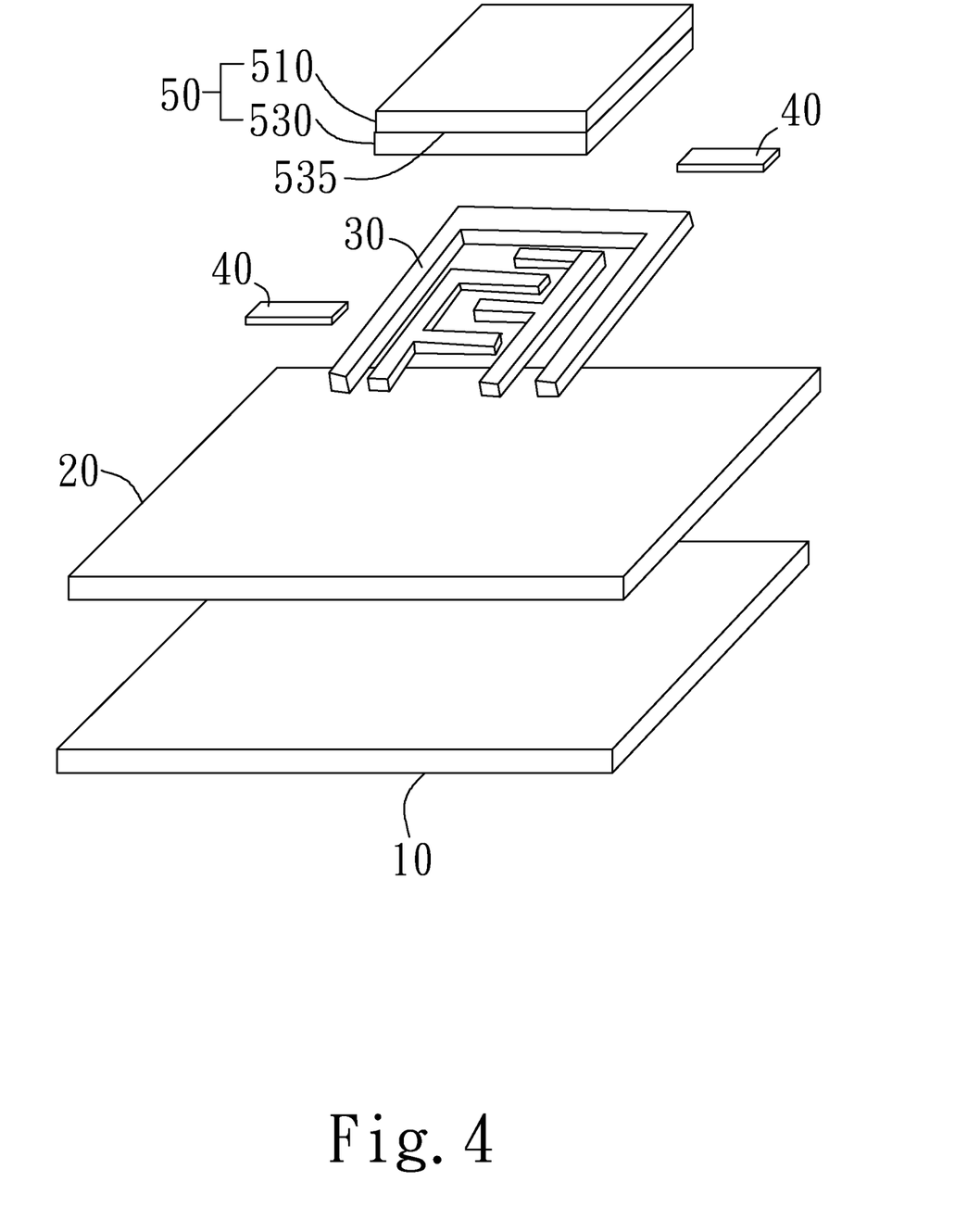
FIG. 4 shows a side exploded view according to the second embodiment of the present invention.

Next, please refer to FIG. 4, which shows a side exploded view according to the second embodiment of the present invention. As shown in the figure, the present invention provides a substrate 10 and a dielectric layer 20. The dielectric layer 20 is disposed on the substrate 10 and includes a heating device 30 and two electrodes 40. A sensing layer 50 is disposed on the heating device 30 and connected with the two electrodes 40. The sensing layer 50 is formed by a first metal oxide layer 510 and a second metal oxide layer 530. The first metal oxide layer 510 is disposed on the second metal oxide layer 530. In addition, an interface layer 535 is further sandwiched between the first and second metal oxide layers 510, 530. The first and second metal layers 510, 530 are annealed at 400~600 degrees. After thermal diffusion and phase change, the junction between the first and second metal oxide layers 510, 530 are thermally processed to form the interface layer 535 between the first and second metal oxide layers 510, 530 with a thickness of 20~80 nanometers approximately.

The material of the first metal oxide layer 510 is tungsten oxide; the material of the second metal oxide layer 530 is tin oxide. The material of the first and second metal oxide layers 510, 530 according to the present invention is selected from the group consisting of tungsten oxide, zinc oxide, and tin oxide. The material of tungsten oxide can be tungsten trioxide ($WO_3$); the material of tin oxide can be tin dioxide ($SnO_2$). The surface of the first metal oxide layer 510 is a rough surface 515 for increasing the contact area for sensing gas and reaction efficiency. The first and second metal oxide layers 510, 530 form the sensing layer 50. The thickness of the sensing layer 50 is 0.1~2 um. The structure of the above two metal oxide layers is used for sensing the concentration of ammonia. A nanometer metal layer 60 can be added thereon for catalyzing the surface of the sensing layer 50 and thus increasing the reaction efficiency. Alternatively, the second metal oxide layer 530 can further includes the reaction layer 520 for increasing the detection efficient for gas. When the material of the reaction layer 520 in the miniature gas sensor according to the present invention is lanthanum carbonate, carbon dioxide can be detected. When the oxygen ions ($O^{2-}$) in the air reacts with high-concentration carbon dioxide, carbonate ions ($CO_3^{2-}$) will be formed. At this moment, the carbonate ions will contact and react with the lanthanum carbonate in the reaction layer 520 to produce lanthanum carbonate, oxygen, carbon dioxide, and ionized electrons. Then the ionized electrons will increase the surface conductivity of the sensing layer 50 and reduce the resistivity. Because the resistance will drop as the ambient concentration of carbon dioxide increases, the ambient concentration of carbon dioxide can be estimated according to the change in resistance and thus achieving the purpose of the gas sensor. Besides, the interface layer 535 according to the present embodiment is formed between the first metal oxide layer 510, which is tungsten oxide, and the second metal oxide layer 530, which is tin oxide, by thermal treatment. By analyzing the vertical elements between the first and second metal oxide layers 510, 530 using secondary ion mass spectrometry (SIMS), the existence of the interface layer 535 having two compounds is verified. The two compounds include tungsten oxide and tin oxide with a thickness of 20~80 nm approximately. Thanks to the interface layer 535, the first and second metal oxide layers 510, 530 are combined more closely. It also facilitates conduction of electrons to the electrode 40 at the bottom layer. With the conduction of the interface layer 535, the concentration of ammonia can be detected more effectively.

The substrate 10 in the miniature gas sensor according to the present invention is used for carrying the semiconductor miniature gas sensor. To maintain the fundamental physical properties of substrate material during the manufacturing process, the substrate material with stability in high-temperature ambient is selected. In addition, to avoid influences of substrate material on the conductivity of the overall chip structure and misleading the conductivity of gas sensing, the substrate material is non-conductive. Based on the above properties, the substrate 10 provided by the present invention can be further selected from the group consisting of glass, silicon, and quartz.

The dielectric layer 20 in the miniature gas sensor according to the present invention is used for electrical isolation for the multilayer structure of semiconductor and increasing the sensing efficiency of the miniature gas sensor. The material of the dielectric layer 20 is an insulator in most cases. When an external electric field is applied, the electrons, ions, or molecules therein will be polarized and thus increasing the electrical capacity of the miniature gas sensor. Based on the above property, the dielectric layer 20 provided by the present invention can be further selected from the group consisting of silicon nitride, silicon oxide, and silicon oxynitride. Preferably, silicon nitride and silicon oxide are adopted and silicon nitride is coated on silicon oxide.

The dielectric layer 20 according to the present invention includes a heating device 30 and two electrodes 40 buried in the dielectric layer 20. Alternatively, they can be disposed on the dielectric layer 20 directly. The heating device 30 is connected with a power supply for receiving the electric power from the power supply and converting it to heat for the gas sensor according to the present invention. To supply stable heat, the material of the heating device 30 according to the present invention is mainly noble metals. Based on the above properties, the material of the heating device 30 is selected from the group consisting of titanium, platinum, gold, silver, and tantalum. In addition, the two electrodes 40 are electrically isolated from the heating device 30 and connected with the sensing layer 50 for measuring the changes in current and voltage of the sensing layer 50 produced by reactions and thus judging the ambient gas concentration.

The sensing layer 50 in the miniature gas sensor according to the present invention is used for contact and react with the target gas in the monitored environment. When the target gas contacts and reacts with the material of the sensing layer 50, the produced ionized electrons will change the potential of the sensing layer 50 and producing current. The two electrodes 40 connected with the sensing layer 50 perform measurement for sensing the gas. The sensing layer 50 includes a first metal oxide layer 510 and a reaction layer 520. The material of the reaction layer 520 and the reaction with the target gas have been described in the above. Hence, the details will not be repeated. In addition, the first metal oxide layer 510 according to the present invention is used as a conductor for conducting electrons. To make the function of transporting electrons more rapidly and agilely, the first metal oxide layer 510 according to the present invention adopts a single material. Based on the above description, the first metal oxide layer 510 according to the present invention is selected from the group consisting of tungsten oxide, zinc oxide, and tin oxide. The material of tungsten oxide can be tungsten trioxide ($WO_3$); the material of tin oxide can be tin dioxide ($SnO_2$).

Figure 5:
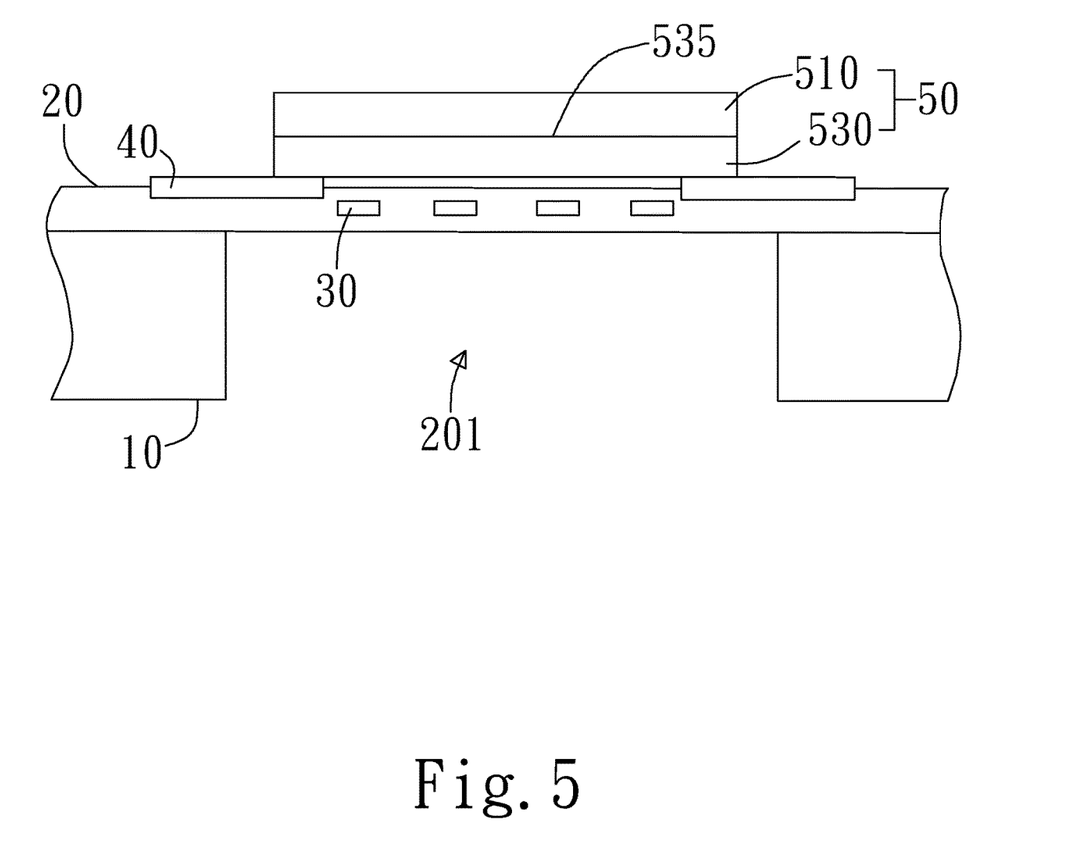
FIG. 5 shows a cross-sectional view according to the second embodiment of the present invention.

Please refer to FIG. 5, which shows a cross-sectional view according to the second embodiment of the present invention. As shown in the figure, the substrate 10 of the gas sensor is a discontinuous structure. By using the design, the dielectric layer 20 is disposed on the substrate 10 with hollow portions and producing a heat dissipating region 201 not contacting directly with the substrate 10. Thanks to the heat dissipating region 201, while the dielectric layer 20 is sensing gas, the heat generated by the heating device 30 can be regulated effectively and avoiding the overall temperature of the gas sensor from being too high. Consequently, the thermal electric effect can be reduced and the measurement stability and accuracy of the gas sensor can be enhanced.

Embodiment 3: Property Test on Gas Sensor Having Two Metal Oxide Layers

Figure 6:
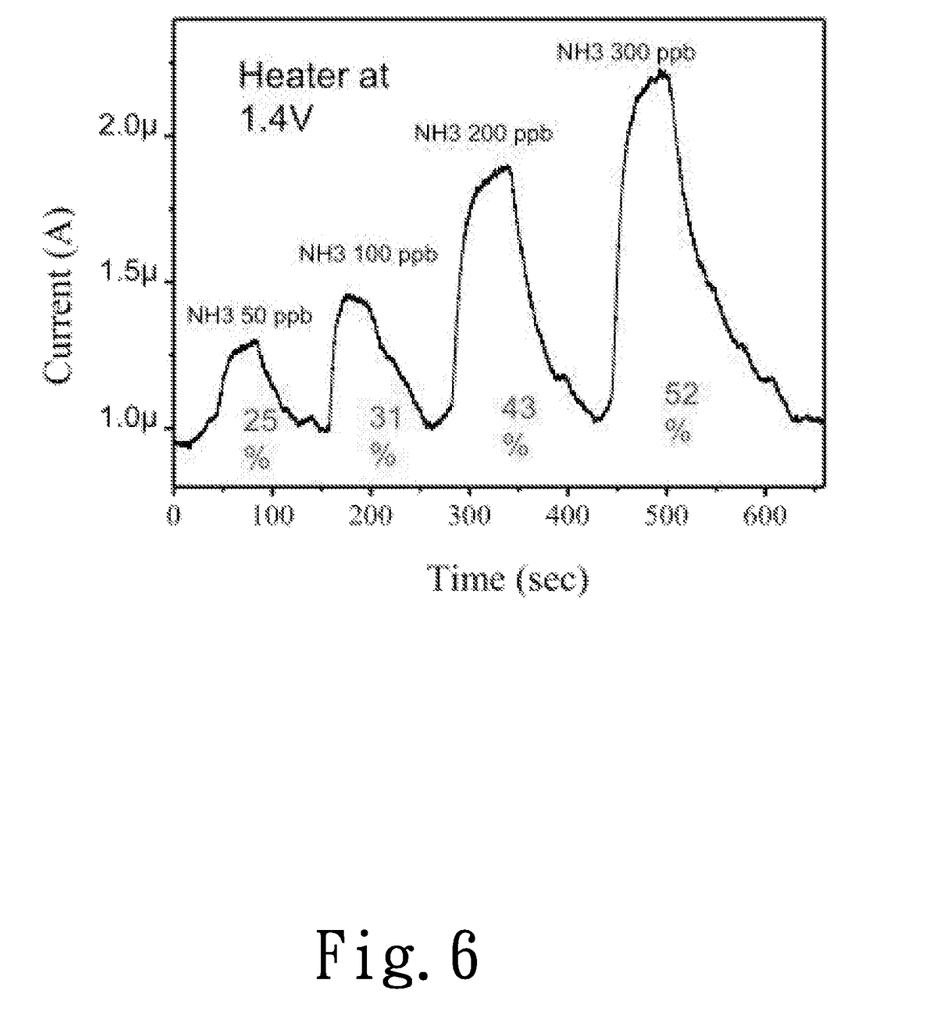
FIG. 6 shows a schematic diagram of the performance of the gas sensor according to the second embodiment of the present invention.

Please refer to FIG. 6, which shows a schematic diagram of sensing time and resistance change while sensing ammonia using a miniature gas sensor according to the present invention having the first metal oxide layer 510 and the second metal oxide layer 530. As shown in the figure, in the first 100 seconds, the ambient concentration of ammonia is 50 ppb. In the next 500 seconds, the ambient concentration of ammonia is increased three times. Each time, the ambient concentration of ammonia is increased by 100 ppb. Observe the current change in the miniature gas sensor having the first metal oxide layer 510 and the second metal oxide layer 530. According to the figure, each time the ambient concentration of ammonia is increased, the current of the gas sensor will rise rapidly to a stable value. The stable value is maintained until the next increase of ambient concentration of ammonia. The difference between the initial and final current values can reach 0.000001 Amperes. It is apparent that the sensing capability if the gas sensor is stable and its sensing range is broad.

Figure 7:
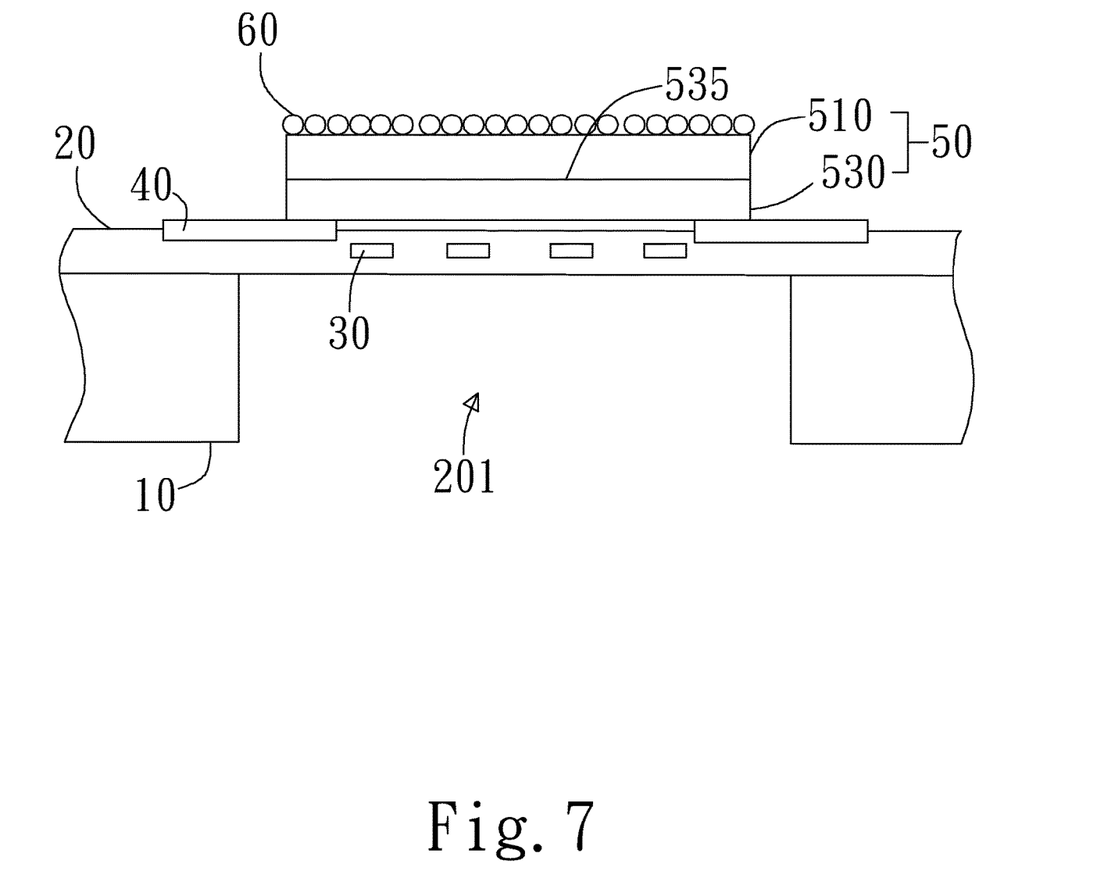
FIG. 7 shows a cross-sectional view according to the third embodiment of the present invention.

Please refer to FIG. 7, which shows a cross-sectional view according to the third embodiment of the present invention. As shown in the figure, the present invention provides a substrate 10 and one or more dielectric layer 20. The dielectric layer 20 is disposed on the substrate 10 and includes a heating device 30 and two electrodes 40. Next, a sensing layer 50 is disposed on the heating device 30 and connected with the two electrodes 40. Besides, the sensing layer 50 is formed by one or more first metal oxide layer 510. The thickness of the dielectric layer 20 is between 2000 and 25000 angstroms; the stress of the dielectric layer 20 is between 1 MPa and 20 MPa.

The material of the sensing layer 50 can be tungsten oxide, tin oxide, or zinc oxide. The material of tungsten oxide can be tungsten trioxide ($WO_3$); the material of tin oxide can be tin dioxide ($SnO_2$). The surface of the sensing layer 50 is a rough surface 515 for increasing the contact area for sensing gas and reaction efficiency. In addition, the sensing layer 50 further includes a nanometer metal layer 60 disposed on the surface. The material of the nanometer metal layer is selected from the group consisting of titanium, gold, platinum, palladium, silver, and tantalum. The structure of the above sensing layer 50 can be used for detecting the concentration of ammonia. The rough surface 515 on the first metal layer 510 of the sensing layer 50 and the structure of nanometer metal layer 60 are used for enhancing the efficiency for sensing ammonia.

The dielectric layer 20 is used for electrical isolation for the multilayer structure of semiconductor and increasing the sensing efficiency of the miniature gas sensor. The material of the dielectric layer 20 is an insulator in most cases. When an external electric field is applied, the electrons, ions, or molecules therein will be polarized and thus increasing the electrical capacity of the miniature gas sensor. Based on the above property, the dielectric layer 20 provided by the present invention can be further selected from the group consisting of silicon nitride, silicon oxide, and silicon oxynitride. Preferably, silicon nitride and silicon oxide are adopted and silicon nitride is coated on silicon oxide. Disposing the dielectric layer 20 on the substrate 10 avoids the sensing layer 50 in the dielectric layer 20 from breakage. Besides, the substrate 10 is a discontinuous structure. By using the design, the dielectric layer 20 is disposed on the substrate 10 with hollow portions and producing a heat dissipating region 201 not contacting directly with the substrate 10. Thanks to the hollow structure, wrinkles or nonuniform heating can be prevented. When the dielectric layer 20 include two or more layers, the compressive and tensile stress on the dielectric layer 20 can be balanced by the dual-layer dielectric layer 20, making the residual stress in the dual-layer dielectric layer 20 smaller than in a single-layer dielectric layer 20.

To sum up, the present invention provides a miniature gas sensor with high stability and the method for manufacturing the same. By disposing a sensing layer with different materials on a semiconductor structure, various ambient gas can be detected. The present invention discloses using lanthanum carbonate to detect carbon dioxide and nanometer gold to detect carbon monoxide. The gas sensor according to the present invention adopts the semiconductor fabrication technology to shrink the volume of gas sensor, and solving the problems of large size, high price, and difficulty in miniaturization for current gas sensors, in particular, carbon-dioxide gas sensors. By reducing the volume of gas sensors effectively, the applicability will be broadened. In addition, by using tungsten oxide, tin oxide, and zinc oxide as the sensing material in the semiconductor gas sensor, ammonia can be sensed. As evident in the embodiments, the sensitivity and accuracy of gas sensors can be improved effectively.

Accordingly, the present invention conforms to the legal requirements owing to its novelty, nonobviousness, and utility. However, the foregoing description is only embodiments of the present invention, not used to limit the scope and range of the present invention. Those equivalent changes or modifications made according to the shape, structure, feature, or spirit described in the claims of the present invention are included in the appended claims of the present invention.

What is claimed is:

1. A miniature gas sensor, comprising a substrate, a dielectric layer, and a sensing layer, said dielectric layer disposed on said substrate, a heating device and two electrodes buried in said dielectric layer and electrically isolated from each other, said sensing layer disposed on said heating device and connected with said two electrodes, wherein said sensing layer is formed by a first metal oxide layer and a reaction layer, said reaction layer is disposed on said first metal oxide layer and the surface of said reaction layer is a rough surface to increase the contact area of said reaction layer for sensing gas, part of said electrodes is extended toward the top of said dielectric layer and supports said sensing layer to separate said sensing layer from said dielectric layer; wherein said first metal oxide layer is used as a conductor for conducting electrons of said sensing layer.

2. The miniature gas sensor of claim 1, wherein said heating device and said two electrodes are further disposed on said dielectric layer.

3. The miniature gas sensor of claim 1, wherein said substrate is a discontinuous structure such that said dielectric layer is disposed on said substrate with hollow portions and producing a heat dissipating region not contacting directly with said substrate.

4. The miniature gas sensor of claim 1, wherein the material of said reaction layer is selected from the group consisting of lanthanum carbonate and nanometer gold.

5. The miniature gas sensor of claim 1, wherein the material of said first metal oxide layer is selected from the group consisting of tungsten oxide, zinc oxide, and tin oxide, and the material of tungsten oxide is tungsten trioxide and the material of tin oxide is tin dioxide.

6. The miniature gas sensor of claim 1, wherein the material of said heating device is selected from the group consisting of titanium, gold, platinum, silver, and tantalum.

7. The miniature gas sensor of claim 1, wherein the material of said dielectric layer is selected from the group consisting of silicon nitride, silicon oxide, and silicon oxynitride.

8. A miniature gas sensor, comprising a substrate, a dielectric layer, and a sensing layer, said dielectric layer disposed on said substrate, a heating device and two electrodes buried in said dielectric layer and electrically isolated from each other, said sensing layer disposed on said heating device and connected with said two electrodes, and said sensing layer is formed by a first metal oxide layer, a second metal oxide layer and a reaction layer disposed on the second metal oxide layer, wherein part of said electrodes is extended toward the top of said dielectric layer and supports said sensing layer to separate said sensing layer from said dielectric layer, said first metal oxide layer is disposed on said second metal oxide layer, and an interface layer is sandwiched between said first metal oxide layer and said second metal oxide layer to facilitate the conduction of electrons to said electrodes at said second metal oxide layer; the material of said first metal oxide layer and said second metal oxide layer is selected from the group consisting of zinc oxide, tungsten oxide, and tin oxide; and the material of tungsten oxide is tungsten trioxide and the material of tin oxide is tin dioxide.

9. The miniature gas sensor of claim 8, wherein the surface of said first metal oxide layer is a rough surface.

10. The miniature gas sensor of claim 8, wherein said heating device and said two electrodes are further disposed on said dielectric layer.

11. The miniature gas sensor of claim 8, wherein said substrate is a discontinuous structure such that said dielectric layer is disposed on said substrate with hollow portions and producing a heat dissipating region not contacting directly with said substrate.

12. The miniature gas sensor of claim 8, wherein the material of said heating device is selected from the group consisting of titanium, gold, platinum, silver, and tantalum.

13. The miniature gas sensor of claim 8, wherein the material of said dielectric layer is selected from the group consisting of silicon nitride, silicon oxide, and silicon oxynitride.

14. The miniature gas sensor of claim 8, wherein said first metal oxide layer further includes a nanometer metal layer on the surface of the first metal oxide layer.

15. The miniature gas sensor of claim 8, wherein said interface layer is formed by thermal diffusion and phase change in the tungsten oxide and tin oxide of said first metal oxide layer and said second metal oxide layer.

16. A miniature gas sensor, comprising a substrate, two dielectric layers, and a sensing layer, said dielectric layer disposed on said substrate, a heating device and two electrodes buried in said dielectric layer and electrically isolated from each other, said sensing layer disposed on said heating device and connected with said two electrodes, wherein said sensing layer is formed by at least one metal oxide layer and a reaction layer disposed on said at least one metal oxide layer, the stress of said two dielectric layers are between 1 MPa and 20 MPa, the compressive and tensile stress on said two dielectric layers are balanced by said two dielectric layers, part of said electrodes is extended toward the top of said dielectric layer and supports said sensing layer to separate said sensing layer from said dielectric layer.

17. The miniature gas sensor of claim 16, wherein the material of said sensing layer is tin oxide or tungsten oxide, and the material of tungsten oxide can be tungsten trioxide and the material of tin oxide can be tin dioxide.

18. The miniature gas sensor of claim 16, wherein the material of said dielectric layer is selected from the group consisting of silicon nitride, silicon oxide, and silicon oxynitride.

19. The miniature gas sensor of claim 16, wherein the surface of said at least one metal oxide layer is a rough surface.

20. The miniature gas sensor of claim 16, wherein said at least one metal oxide layer further includes a nanometer metal layer on the surface.

21. The miniature gas sensor of claim 20, wherein the material of said nanometer metal layer is selected from the group consisting of titanium, gold, platinum, silver, palladium, and tantalum.

22. The miniature gas sensor of claim 16, wherein the thickness of said dielectric layer is between 2000 and 25000 angstroms.

\* \* \* \* \*